(12) United States Patent
Yasuda et al.

(10) Patent No.: US 12,369,881 B2
(45) Date of Patent: Jul. 29, 2025

(54) BLOOD FLOW IMAGE FORMING DEVICE AND BLOOD FLOW IMAGE FORMING PROGRAM

(71) Applicant: FUJIFILM Healthcare Corporation, Kashiwa (JP)

(72) Inventors: Jun Yasuda, Chiba (JP); Tomohiko Tanaka, Chiba (JP); Tetsuya Yamada, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 262 days.

(21) Appl. No.: 18/224,757

(22) Filed: Jul. 21, 2023

(65) Prior Publication Data

US 2024/0032888 A1     Feb. 1, 2024

(30) Foreign Application Priority Data

Jul. 29, 2022 (JP) ................. 2022-121890

(51) Int. Cl.
*A61B 8/06* (2006.01)
*A61B 8/00* (2006.01)

(52) U.S. Cl.
CPC .............. *A61B 8/06* (2013.01); *A61B 8/488* (2013.01)

(58) Field of Classification Search
CPC .. A61B 8/06; A61B 8/488; A61B 8/08; A61B 8/463; A61B 8/5207; A61B 8/5223; A61B 8/469; A61B 8/5269; A61B 8/0891; A61B 8/5215; G06T 7/194
See application file for complete search history.

(56) References Cited

FOREIGN PATENT DOCUMENTS

| JP | 2009-261436 A | 11/2009 |
|----|---------------|---------|
| JP | 2021-104301 A | 7/2021  |

*Primary Examiner* — Boniface N Nganga
(74) *Attorney, Agent, or Firm* — Paul Teng

(57) ABSTRACT

The array of reception beam data sets obtained by transmitting and receiving ultrasonic waves to and from a subject constitutes a two-dimensional data space. Based on the Doppler signals, a distribution data calculation unit calculates, for each of data elements in the two-dimensional data space, at least one of power of the Doppler signal, the velocity of tissue in the subject, and the velocity dispersion of tissue in the subject. A discrimination index map generation unit generates a discrimination index map indicating the likelihood of being a blood flow region A in the two-dimensional data space composed of the array of reception beam data sets, based on distribution data that are set for each of regions of interest in the two-dimensional data space. Based on the Doppler signal and the discrimination index map, a blood flow image forming unit forms a blood flow image with reduced blooming artifacts.

8 Claims, 13 Drawing Sheets

BLOOD FLOW IMAGE FORMING DEVICE AND BLOOD FLOW IMAGE FORMING PROGRAM

CROSS REFERENCE TO RELATED APPLICATION

This application claims priority to Japanese Patent Application No. 2022-121890 filed on Jul. 29, 2022, which is incorporated herein by reference in its entirety including the specification, claims, drawings, and abstract.

TECHNICAL FIELD

The present specification discloses improvements to a blood flow image forming device and a blood flow image forming program.

BACKGROUND

An ultrasonic diagnostic device is a device that transmits ultrasonic waves toward a subject, receives waves reflected from a scatterer (for example, tissue in the subject), and forms an ultrasonic image based on the received reflected waves. The ultrasonic diagnostic device can form various types of ultrasonic images. For example, the ultrasonic diagnostic device can form an ultrasonic tomographic image (B-mode image) by measuring the distance to the scatterer based on the time required for transmitting and receiving waves and the speed of sound and then converting the signal intensity (sound pressure) of the reflected waves into luminance values.

Among ultrasonic images, Doppler images represent movement of tissue in a living body, which is the subject. Types of Doppler images include a color Doppler image obtained by means of a technique called color Doppler imaging (CDI) where colors are used to represent the direction and velocity of movement of tissue in the living body, and a power image where colors and the brightness of the colors are used to represent power which is the signal intensity of a Doppler signal. The Doppler image is formed based on the Doppler effect. Specifically, first, an ultrasound probe transmits and receives ultrasonic waves (transmits and receives packets) multiple times to and from a blood flow region to obtain received signals. The amount of phase rotation (phase shift) is calculated by autocorrelation between the received signals to detect a Doppler shift. Then, a coloring process is performed according to the intensity and sign of the obtained Doppler shift or the intensity of the Doppler signal, thereby obtaining a blood flow image. The blood flow image is then displayed so as to be superimposed on a B-mode image.

The received signals include Doppler shift signals other than Doppler shift signals from a blood flow, such as those due to tissue motion or reflection, refraction, scattering, or attenuation of an ultrasonic beam by a tissue structure, such as a blood vessel wall. This may cause, in the blood flow image, which is a Doppler image representing the blood flow, an artifact (false image) in which the blood flow appears in a region where there is no blood flow. One type of artifact is a blooming artifact that appears in the lower part of the blood vessel.

Although there are several causes of the blooming artifact, a typical cause will now be described with reference to FIG. 20. The ultrasound probe identifies a position of a scatterer based on the length of time between transmission and reception of ultrasonic waves to and from the scatterer (the length of time can be regarded as the distance between the ultrasound probe and the scatterer, as the velocity of ultrasonic waves is considered to be constant inside the subject). Here, ultrasonic waves transmitted from the ultrasound probe may be reflected by the blood vessel wall (especially, the lower blood vessel wall), and the reflected waves may be further reflected by the blood flow at position S, and the ultrasound probe may receive these reflected ultrasonic waves. The paths of these ultrasonic waves and reflected waves are shown by dash-dot lines in FIG. 20. The ultrasound probe then recognizes the received reflected waves as reflected waves from position S', which is located at a distance half the dash-dot line path in the direction of transmitting the ultrasonic waves. This causes blood flow components originally located at the position S to be rendered at the position S', which results in blooming artifacts.

A technique has been proposed to reduce such artifacts. For example, JP 2021-104301 A discloses a technique of reducing blooming artifacts by automatically setting a power or velocity dispersion threshold for rendering a blood vessel by using statistics of power and velocity dispersion of Doppler signals for all received signals for one frame corresponding to one ultrasonic image.

The technique disclosed in JP 2021-104301 A can reduce the blooming artifacts. However, as the power, velocity, or velocity dispersion of the artifacts varies from location to location even within the same frame, the artifacts may remain even when a uniform threshold is applied to the entire frame. Therefore, new techniques that can reduce blooming artifacts to a larger extent in a blood flow image are desired.

An object of the blood flow image forming device disclosed herein is to further reduce blooming artifacts in a blood flow image, which is a Doppler image representing a blood flow.

CITATION LIST

Patent Literature

Patent Document 1: JP 2021-104301 A

SUMMARY

A blood flow image forming device disclosed in the present specification includes a reception beam data acquisition unit that acquires an array of reception beam data sets generated based on signals received from an ultrasound probe that transmits and receives ultrasonic waves with respect to a beam scanning plane in a subject, the array of reception beam data sets corresponding to transmission beams forming the beam scanning plane, a distribution data calculation unit that calculates, for each of a plurality of regions of interest that are set in a two-dimensional data space composed of the array of reception beam data sets, distribution data that relate to at least one of power distribution of a Doppler signal obtained from the reception beam data set, velocity distribution of tissue in the subject, and velocity dispersion distribution of tissue in the subject, based on the array of reception beam data sets, a discrimination index map generation unit that generates a discrimination index map indicating the likelihood of being a blood flow region in the two-dimensional data space based on the distribution data for each of the regions of interest, and a blood flow image forming unit that forms a blood flow image in which a blood flow in the subject is represented based on the Doppler signal obtained from the array of reception beam data sets and the discrimination index map.

The two-dimensional data space composed of the array of reception beam data sets is conceptually divided into the blood flow region corresponding to the blood flow (blood vessel), a background region corresponding to the tissue in the subject other than the blood flow, and a blooming region that is below the blood flow region and generates blooming artifacts in the Doppler image. The distribution data for the region of interest set in the blood flow region, the distribution data for the region of interest set in the background region, and the distribution data for the region of interest set in the blooming region have different characteristics from one another. It is thus possible to generate a discrimination index map indicating the likelihood of being the blood flow region in the two-dimensional data space based on the distribution data for each of the regions of interest. This discrimination index map makes it possible to discriminate the blood flow region from other regions (that is, the background region and the blooming region). In other words, it is thus possible to form a blood flow image with reduced blooming artifacts based on the discrimination index map.

The discrimination index map generation unit may generate the discrimination index map based on variation in power around a most frequently occurring value in the power distribution for each of the regions of interest, variation in velocity around a most frequently occurring value in the velocity distribution for each of the regions of interest, or variation in dispersion around a most frequently occurring value in the dispersion distribution for each of the regions of interest.

The distribution data for the region of interest set in the blood flow region differ from the distribution data for the regions of interest set in the other regions, especially in the variation in power around the most frequently occurring power value, the variation in velocity around the most frequently occurring velocity value, or the variation in velocity dispersion around the most frequently occurring velocity dispersion value. The above configuration thus makes it possible to generate a discrimination index map that can more accurately discriminate the blood flow region from the other regions.

The discrimination index map generation unit may normalize a discrimination index included in the discrimination index map, and the blood flow image forming unit may form the blood flow image based on the Doppler signal and the discrimination index map having the normalized discrimination index.

This configuration makes it possible to properly discriminate the blood flow region from the other regions (the background region and the blooming region) (that is, to obtain the blood flow image with reduced blooming artifacts), even when the discrimination index for a certain region of interest is considerably larger than those for the other regions of interest.

Parameters for the process of forming the blood flow image, including parameters representing the size of the region of interest and parameters for the normalization, may be configurable by the user.

This configuration enables the user to adjust the degree of reduction of blooming artifacts in the blood flow image.

The blood flow image forming device may further include a display control unit that displays the discrimination index map on the display unit.

This configuration enables the user to confirm the discrimination index map which has been used to reduce the blooming artifacts.

The blood flow image forming device disclosed in the present specification may include a reception beam data acquisition unit that acquires an array of reception beam data sets generated based on signals received from an ultrasound probe that transmits and receives ultrasonic waves with respect to a beam scanning plane in a subject, the array of reception beam data sets corresponding to transmission beams forming the beam scanning plane, a distribution data calculation unit that calculates, for each of a plurality of regions of interest that are set in a two-dimensional data space composed of the array of reception beam data sets, power distribution of a Doppler signal obtained from the reception beam data set, velocity distribution of tissue in the subject, and velocity dispersion distribution of tissue in the subject, based on the array of reception beam data sets, a discrimination index map generation unit that generates a discrimination index map indicating the likelihood of being a blood flow region in the two-dimensional data space based on the power distribution, the velocity distribution, and the dispersion distribution, and a blood flow image forming unit that forms a blood flow image in which a blood flow in the subject is represented based on the Doppler signal obtained from the array of reception beam data sets and the discrimination index map.

In addition, a blood flow image forming program disclosed in the present specification allows a computer to function as a reception beam data acquisition unit that acquires an array of reception beam data sets generated based on signals received from an ultrasound probe that transmits and receives ultrasonic waves with respect to a beam scanning plane in a subject, the array of reception beam data sets corresponding to transmission beams forming the beam scanning plane, a distribution data calculation unit that calculates, for each of a plurality of regions of interest that are set in a two-dimensional data space composed of the array of reception beam data sets, distribution data that relate to at least one of power distribution of a Doppler signal obtained from the reception beam data set, velocity distribution of tissue in the subject, and velocity dispersion distribution of tissue in the subject, based on the array of reception beam data sets, a discrimination index map generation unit that generates a discrimination index map indicating the likelihood of being a blood flow region in the two-dimensional data space based on the distribution data for each of the regions of interest, and a blood flow image forming unit that forms a blood flow image in which a blood flow in the subject is represented based on the Doppler signal obtained from the array of reception beam data sets and the discrimination index map.

The blood flow image forming device disclosed herein makes it possible to further reduce blooming artifacts in a blood flow image which is a Doppler image representing a blood flow.

BRIEF DESCRIPTION OF DRAWINGS

Embodiments of the present disclosure will be described based on the following figures, wherein.

DESCRIPTION OF EMBODIMENTS

Figure 1:
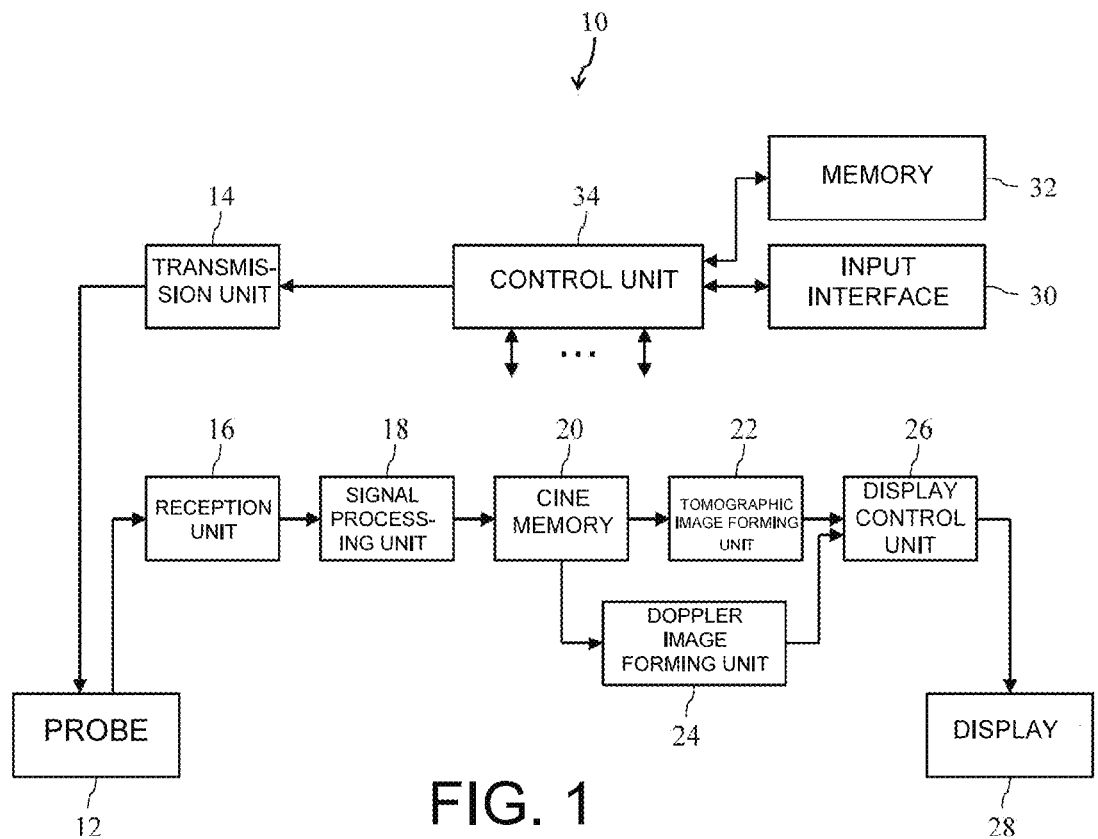
FIG. 1 is a schematic configuration diagram of an ultrasonic diagnostic device according to an embodiment.

FIG. 1 is a schematic configuration diagram of an ultrasonic diagnostic device 10 which is a blood flow image forming device according to an embodiment. The ultrasonic diagnostic device 10 is provided in a medical facility, such as a hospital. The ultrasonic diagnostic device 10 is a device that transmits and receives ultrasonic waves to and from a subject which is a living body and forms and displays an ultrasonic image based on thus obtained received signals.

In particular, the ultrasonic diagnostic device 10 detects a Doppler shift based on the amount of phase shift between the received signals and forms, based on the Doppler shift, a Doppler image that is an ultrasonic image representing the velocity, velocity dispersion, or power of tissue in the subject. Types of Doppler images include a color Doppler image in which the direction and magnitude of the velocity or velocity dispersion of the tissue are represented by colors, and a power image in which power is represented by colors or the like. Power refers to the intensity of a Doppler signal that represents a Doppler shift, and the power image has advantages over the color Doppler image in that, for example, even a slow blood flow can be displayed brightly. Among the Doppler images, a Doppler image representing a blood flow in the subject will herein be referred to as a blood flow image.

A probe 12, which is an ultrasound probe, transmits ultrasonic waves and receives reflected waves. Specifically, the probe 12 is brought into contact with a body surface of the subject to thereby transmit ultrasonic beams to the subject and receives reflected waves from tissue in the subject. The probe 12 contains a transducer element array composed of a plurality of transducer elements. Each transducer element of the array is fed with a transmission signal which is an electrical signal from a transmission unit 14 (described below) to thereby generate an ultrasonic beam (transmission beam). The ultrasonic beam is scanned to form a beam scanning plane in the subject. Each transducer element of the array also receives a reflected wave from the subject, converts the reflected wave into a received signal which is an electrical signal, and transmits the received signal to a reception unit 16 described below.

The transmission unit 14 functions as a transmission beam former. During transmission of ultrasonic waves, the transmission unit 14 supplies a plurality of transmission signals to the probe 12 (specifically, the transducer element array) in parallel. This allows the probe 12 to transmit ultrasonic beams.

The reception unit 16 functions as a reception beam former. During receipt of the reflected waves, the reception unit 16 receives, in parallel, a plurality of reception signals respectively corresponding to the transmission beams forming the beam scanning plane from the probe 12 (specifically, the array of transducer elements). The reception unit 16 performs phasing addition or the like on the plurality of reception signals, thereby generating a plurality of reception beam data sets (array of reception beam data sets). In the present embodiment, the reception unit 16 thus corresponds to a reception beam data acquisition unit. Each reception beam data set is composed of a plurality of signals (data pieces) that are arranged in the depth direction of the subject and indicate the signal intensity of the reflected wave. In other words, the array of reception beam data sets can define a two-dimensional data space that extends in the depth direction and the azimuth direction (the scanning direction of the transmission beam). A single B-mode image is formed by converting the signal intensity of the array of reception beam data sets (herein referred to as a reception frame data set) obtained from the entire beam scanning plane into luminance values. The data pieces of the array of reception beam data sets corresponding to pixels of the B-mode image will be referred to herein as data elements.

A signal processing unit 18 performs various signal processing techniques on each reception beam data set from the reception unit 16 including, for example, detection processing, logarithmic amplification processing, gain correction processing, and filtering processing.

A cine memory 20 is a memory that stores a plurality of reception frame data sets processed by the signal processing unit 18. The cine memory 20 is a first-in-first-out (FIFO) buffer that outputs the reception frame data sets input from the signal processing unit 18 in the order in which they are input.

A tomographic image forming unit 22 forms an ultrasonic tomographic image (that is, a B-mode image) based on the reception frame data set input from the cine memory 20. Specifically, the tomographic image forming unit 22 forms the B-mode image by converting the signal intensity of data elements of the reception beam data sets contained in the reception frame data set into luminance values.

A Doppler image forming unit 24 forms a Doppler image based on a Doppler shift between reception signals obtained by transmitting and receiving ultrasonic waves to and from the subject. The process performed by the Doppler image forming unit 24 will be described in detail below.

A display control unit 26 displays the B-mode image formed by the tomographic image forming unit 22 on a display 28 that is a display unit composed of, for example, an LCD panel. The display control unit 26 also superimposes the Doppler image formed by the Doppler image forming unit 24 on the B-mode image formed by the tomographic image forming unit 22 and displays the resulting image on the display 28.

An input interface 30 is composed of, for example, buttons, a trackball, or a touch panel. The input interface 30 is used to input user commands to the ultrasonic diagnostic device 10.

A memory 32 is composed of, for example, a hard disk drive (HDD), solid state drive (SSD), embedded Multi Media Card (eMMC), read-only memory (ROM), or random-access memory (RAM). The memory 32 stores a blood flow image forming program for operating the units of the ultrasonic diagnostic device 10. The blood flow image forming program can be stored in a computer-readable non-transient storage medium, such as a universal serial bus (USB) memory or CD-ROM. The ultrasonic diagnostic device 10 can read the blood flow image forming program from such a storage medium and execute it.

A control unit 34 includes at least one of, for example, a general-purpose processor (for example, central processing unit (CPU)) and a dedicated processor (for example, graphics processing unit (GPU), application specific integrated circuit (ASIC), field programmable gate array (FPGA), or programmable logic device). The control unit 34 may be configured by cooperation of a plurality of processing devices that are physically located at a distance from one another, rather than being composed of a single processing unit. The control unit 34 controls the units of the ultrasonic diagnostic device 10 according to the ultrasonic image processing program stored in the memory 32.

Each of the transmission unit 14, the reception unit 16, the signal processing unit 18, the tomographic image forming unit 22, the Doppler image forming unit 24, and the display control unit 26 is composed of one or more processors, chips, electrical circuits, and the like. Each of these units may be implemented by cooperation of hardware and software.

Figure 2:
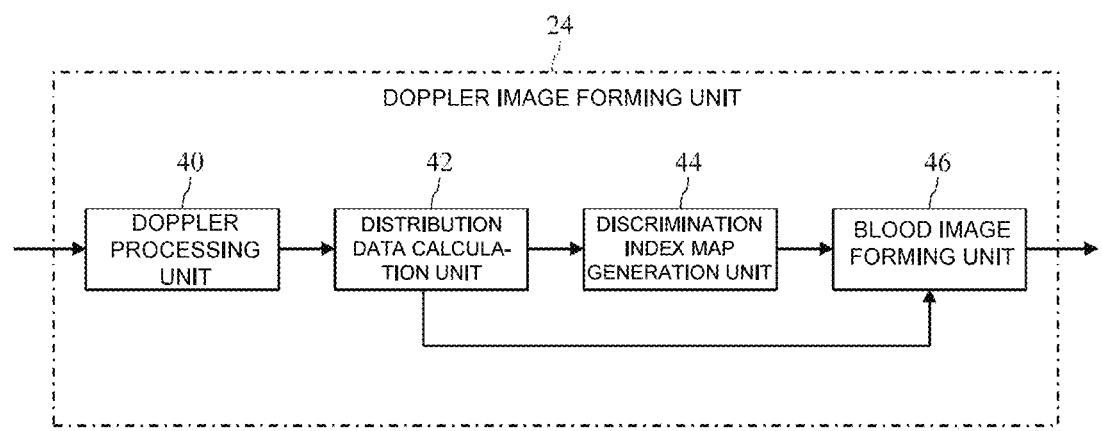
FIG. 2 is a schematic configuration diagram of a Doppler image forming unit.

FIG. 2 is a schematic configuration diagram of the Doppler image forming unit 24. As shown in FIG. 2, the Doppler image forming unit 24 functions as a Doppler processing unit 40, distribution data calculation unit 42, discrimination index map generation unit 44, and blood flow image forming unit 46.

The Doppler processing unit 40 performs, for example, orthogonal detection processing of decomposing the reception beam data set received from the cine memory 20 into complex signals (real part signal (I component) and imaginary part signal (Q component)), filter processing of applying to the complex signals obtained by the orthogonal detection processing a wall filter for removing noise (clutter component) caused by body motion of the subject and the like, and autocorrelation calculation of calculating the correlation between the I component and the Q component to obtain the amount of phase shift between the reception beam data sets.

Figure 3:
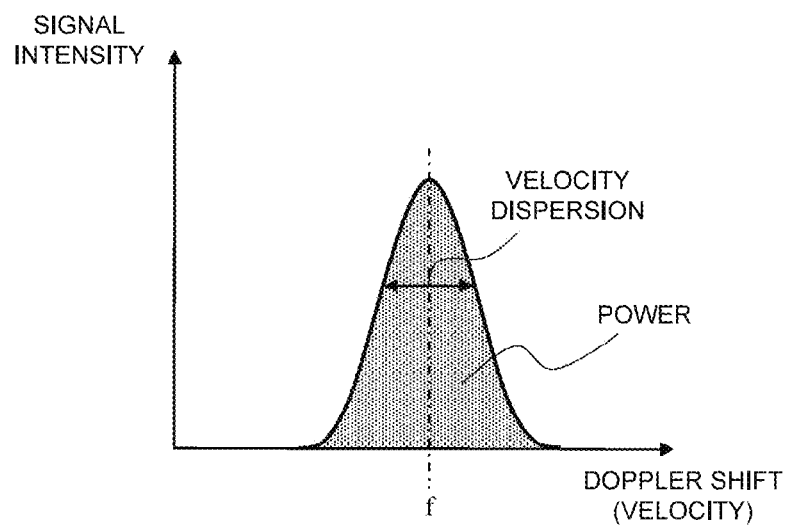
FIG. 3 is a conceptual diagram showing an example of a Doppler signal.

A signal of the reception beam data set obtained after the processing by the Doppler processing unit 40 will herein be referred to as a Doppler signal. More specifically, a signal obtained after the orthogonal detection processing and the autocorrelation calculation contains a mixture of tissue and blood flow components, and applying the wall filter to this signal allows to extract only the blood flow component and obtain the Doppler signal. The Doppler signal is a signal indicating the signal intensity of a Doppler shift (shift frequency) for each data element. FIG. 3 is a graph showing an example of a Doppler signal for a certain data element. In FIG. 3, the horizontal axis represents a Doppler shift (shift frequency), and the vertical axis represents the signal intensity. As shown in FIG. 3, the Doppler signal generally has a signal intensity distribution around the center frequency f. The Doppler processing unit 40 (and the other processing units included in the Doppler image forming unit 24) do not have to process the entire reception frame data, but only a portion of it (for example, a region of interest specified by the user).

The distribution data calculation unit 42 calculates, for each data element, at least one of power of the Doppler signal, the velocity of tissue in the subject, and the velocity dispersion of tissue in the subject, based on the Doppler signal for each data element as shown in FIG. 3. Specifically, the distribution data calculation unit 42 calculates the power of the data element based on an integral value of the signal intensity (colored portion of the graph). In addition, as the Doppler shift having the signal intensity has width, the distribution data calculation unit 42 also calculates, as the velocity of that data element, the average velocity calculated based on the Doppler shift having the signal intensity. The distribution data calculation unit 42 further calculates the velocity dispersion of that data element based on the width of the graph of the Doppler signal.

The distribution data calculation unit 42 thus calculates the power, velocity, or velocity dispersion for each data element, thereby calculating a power map showing the power distribution, a velocity map showing the velocity distribution, or a dispersion map showing the velocity dispersion distribution in the two-dimensional data space composed of the array of reception beam data sets (that is, a group of data elements arranged in two dimensions).

Figure 4:
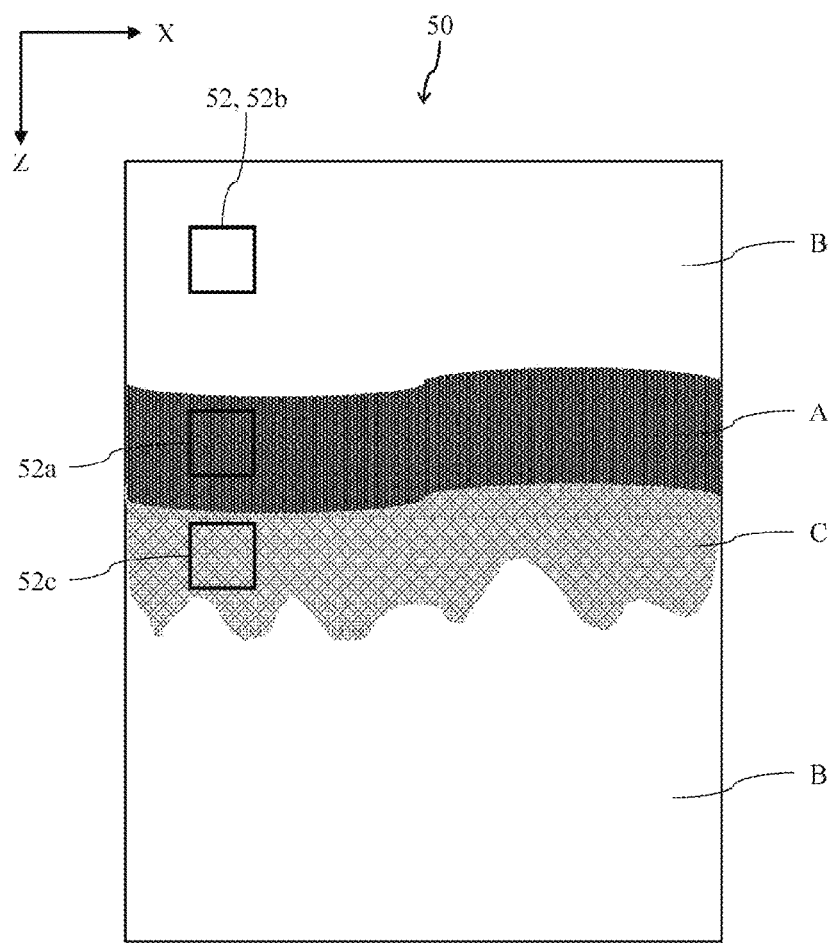
FIG. 4 is a conceptual diagram showing an example of a power map.

FIG. 4 is a conceptual diagram showing an example of a power map 50. In FIG. 4 (and in FIG. 9 described below), the x-axis direction represents the azimuth direction, and the z-axis direction represents the depth direction.

The power map 50 (or velocity map or dispersion map) is conceptually divided into a blood flow region A that corresponds to a blood flow (blood vessel), a background region B that corresponds to tissue in the subject other than the blood flow, and a blooming region C that is under the blood flow region A (that is, on the positive side in the z-axis direction) and generates blooming artifacts in the Doppler image.

The distribution data calculation unit 42 sets a plurality of regions of interest (Region of Interest (ROI)) 52 in the two-dimensional data space (that is, the power map 50, velocity map, or dispersion map) composed of the array of reception beam data sets. In FIG. 4, only some of the plurality of ROIs 52 are illustrated. In particular, the distribution data calculation unit 42 sets the ROIs 52 such that a single ROI 52 contains a plurality of data elements. Then, for each of the plurality of ROIs 52, the distribution data calculation unit 42 can obtain distribution data that is about at least one of power distribution indicating distribution of power, velocity distribution indicating distribution of velocity, or velocity dispersion distribution indicating distribution of velocity dispersion.

The important point here is that characteristics of the distribution data for an ROI 52*a* in the blood flow region A, an ROI 52*b* in the background region B, and an ROI 52*c* in the blooming region C differ from one another.

Figure 5A:
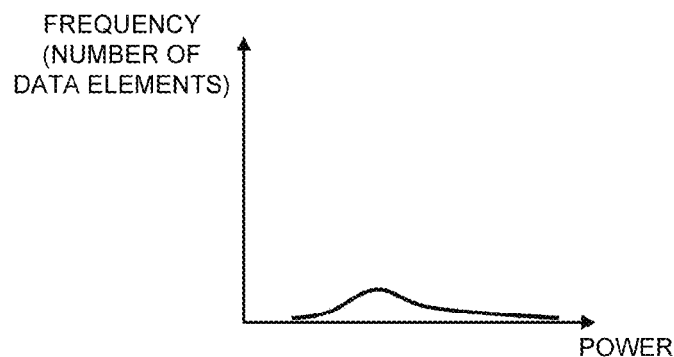
FIG. 5A is a graph showing an example of power distribution in an ROI set in a blood flow region.
Figure 5B:
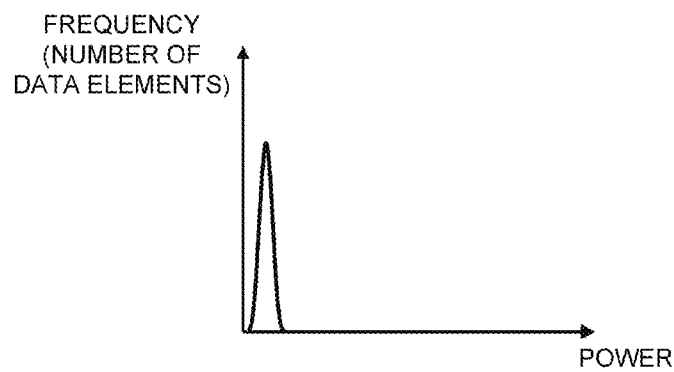
FIG. 5B is a graph showing an example of power distribution in an ROI set in a background region.
Figure 5C:
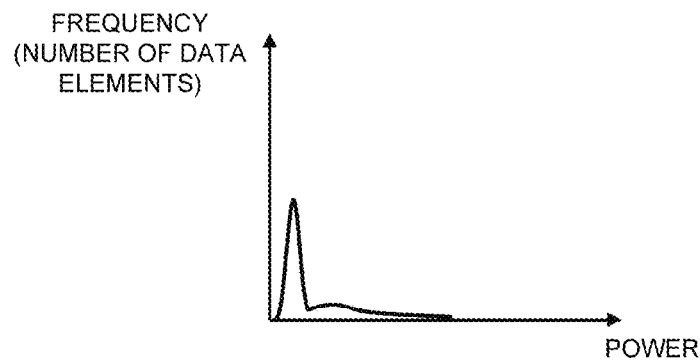
FIG. 5C is a graph showing an example of power distribution in an ROI set in a blooming region.

FIG. 5A is a graph showing an example of power distribution in the ROI 52*a* set in the blood flow region A. FIG. 5B is a graph showing an example of power distribution in the ROI 52*b* set in the background region B. FIG. 5C is a graph showing an example of power distribution in the ROI 52*c* set in the blooming region C. In each of FIG. 5A to the horizontal axis represents power, and the vertical axis represents frequency (number of data elements). In other words, FIGS. 5A to 5C respectively represents histograms of the power in the ROIs 52*a* to 52*c*.

As shown in FIG. 5A, in the power distribution in the ROI 52*a* in the blood flow region A, variation in power is large, and the frequency is not prominent at any particular power level. In other words, this power graph has the shape of a wide and low peak. In contrast, as shown in FIG. 5B, in the power distribution in the ROI 52*b* in the background region B, variation in power is small, and the frequency is prominent at a particular power level (low power level). In other words, this power graph has the shape of a narrow and high peak. The power distribution in the ROI 52*c* in the blooming region C has the characteristics of both the power distributions in the blood flow region A and the background region B. Specifically, as shown in FIG. 5C, the power distribution in the ROI 52*c* in the blooming region C has the shape of the narrow peak where variation in power is small and the frequency is prominent at a particular power level (low power level), along with the wide and low peak (which is lower than the narrow peak).

Figure 6A:
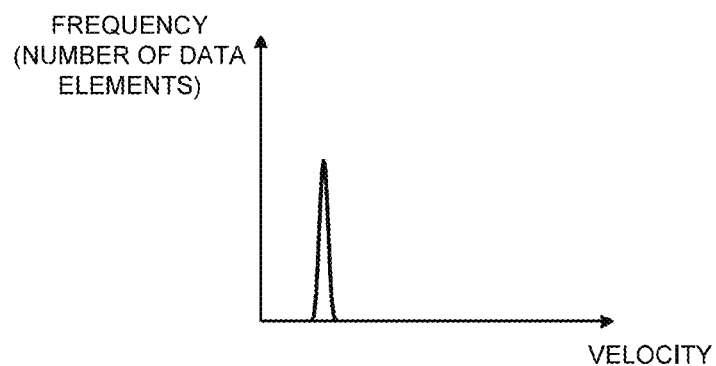
FIG. 6A is a graph showing an example of velocity distribution in the ROI set in the blood flow region.
Figure 6B:
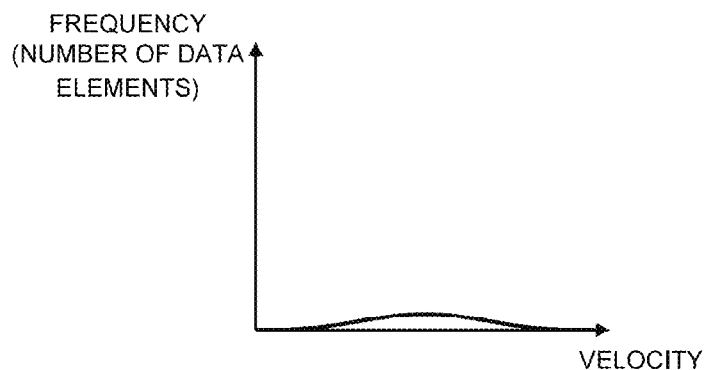
FIG. 6B is a graph showing an example of velocity distribution in the ROI set in the background region.
Figure 6C:
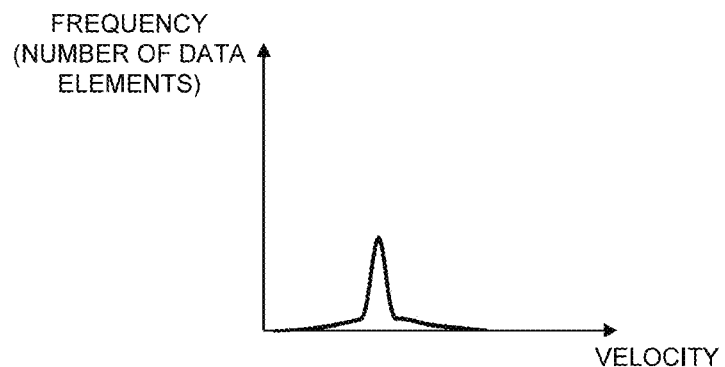
FIG. 6C is a graph showing an example of velocity distribution in the ROI set in the blooming region.

FIG. 6A is a graph showing an example of velocity distribution in the ROI 52*a* in the blood flow region A. FIG. 6B is a graph showing an example of velocity distribution in the ROI 52*b* in the background region B. FIG. 6C is a graph showing an example of velocity distribution in the ROI 52*c* in the blooming region C. In each of FIGS. 6A to 6C, the horizontal axis represents velocity, and the vertical axis represents frequency (number of data elements). In other words, FIGS. 6A to 6C respectively represent histograms of the velocity in the ROIs 52*a* to 52*c*.

As shown in FIG. 6A, in the velocity distribution in the ROI 52*a* in the blood flow region A, variation in velocity is small, and the frequency is prominent at a particular velocity, unlike the power distribution. In other words, this velocity graph has the shape of a narrow and high peak. In addition, as shown in FIG. 6B, in the velocity distribution in the ROI 52*b* in the background region B, variation in velocity is large, and the frequency is not prominent at any particular velocity. In other words, this velocity graph has the shape of a wide and low peak. The velocity distribution in the ROI 52*c* in the blooming region C has the characteristics of both the velocity distributions in the blood flow region A and the background region B. Specifically, as shown in FIG. 6C, the velocity distribution in the ROI 52*c* in the blooming region C has the shape of the narrow peak where variation in velocity is small and the frequency is prominent at a particular velocity, along with the wide and low peak (which is lower than the narrow peak).

Figure 7A:
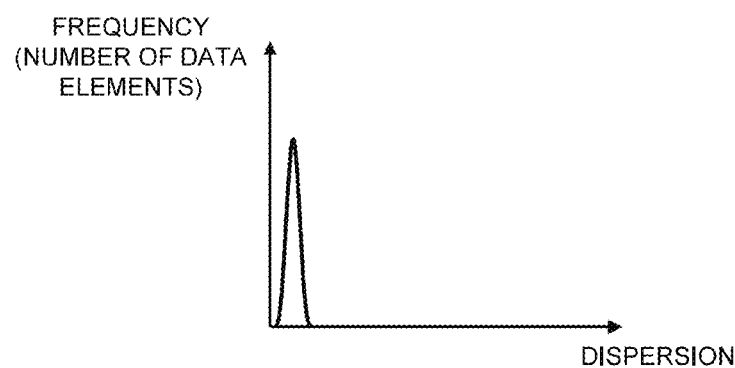
FIG. 7A is a graph showing an example of velocity dispersion distribution in the ROI set in the blood flow region.
Figure 7B:
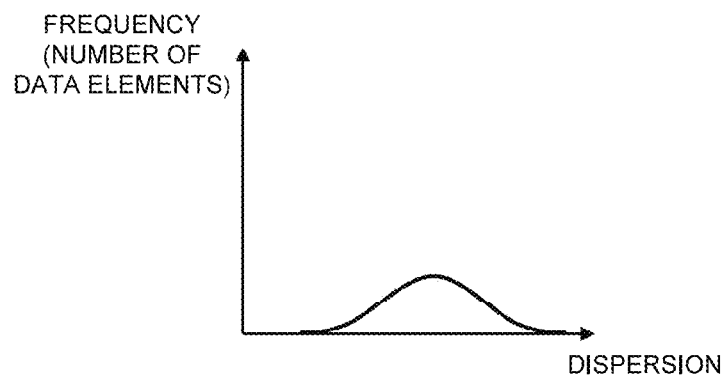
FIG. 7B is a graph showing an example of velocity dispersion distribution in the ROI set in the background region.
Figure 7C:
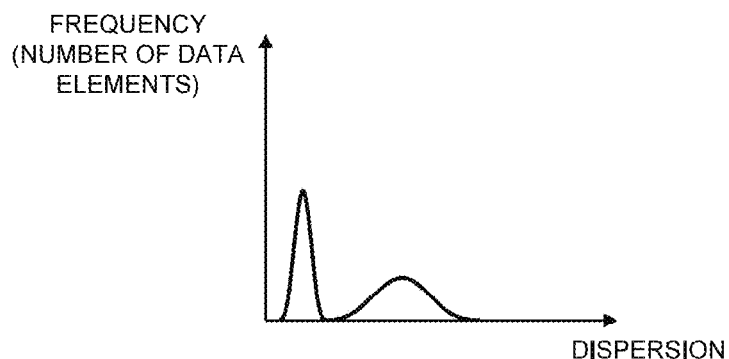
FIG. 7C is a graph showing an example of velocity dispersion distribution in the ROI set in the blooming region.

The velocity dispersion distribution exhibits similar characteristics to the velocity distribution. FIG. 7A is a graph showing an example of velocity dispersion distribution in the ROI 52*a* in the blood flow region A. FIG. 7B is a graph showing an example of velocity dispersion distribution in the ROI 52*b* in the background region B. FIG. 7C is a graph showing an example of velocity dispersion distribution in the ROI 52*c* in the blooming region C. In each of FIGS. 7A to 7C, the horizontal axis represents velocity dispersion, and the vertical axis represents frequency (number of data elements). In other words, FIGS. 7A to 7C respectively represent histograms of the velocity dispersion in the ROIs 52*a* to 52*c*.

As shown in FIG. 7A, in the velocity dispersion distribution in the ROI 52*a* in the blood flow region A, variation in velocity dispersion is small, and the frequency is prominent for a particular velocity dispersion. In other words, this velocity dispersion graph has the shape of a narrow and high peak. In contrast, as shown in FIG. 7B, in the velocity dispersion distribution in the ROI 52*b* in the background region B, variation in velocity dispersion is large, and the frequency is not prominent at any particular velocity dispersion. In other words, this velocity dispersion graph has the shape of a wide and low peak. The velocity dispersion distribution in the ROI 52*c* in the blooming region C has the characteristics of both the velocity dispersion distributions in the blood flow region A and the background region B. Specifically, as shown in FIG. 7C, the velocity dispersion distribution in the ROI 52*c* in the blooming region C has the shape of a narrow peak where variation in velocity dispersion is small and the frequency is prominent at a particular velocity dispersion, along with the wide and low peak (which is lower than the narrow peak).

The discrimination index map generation unit 44 generates a discrimination index map indicating the likelihood of being the blood flow region A in the two-dimensional data space composed of the array of reception beam data sets, based on the distribution data for each of the regions of interest, which is calculated by the distribution data calculation unit 42. Specifically, the discrimination index map is a map generated by assigning a discrimination index indicating the likelihood of being in the blood flow region A to each of the data elements in the two-dimensional data space composed of the array of reception beam data sets. Because, as described above, the characteristics of the distribution data for the ROIs 52 in the blood flow region A, the background region B, and the blooming region C differ from one another, the discrimination index map generation unit 44 assigns to each of the ROIs 52 (more accurately, data elements constituting each ROI 52) a discrimination index (value) indicating the likelihood that that ROI 52 is within the blood flow region A, based on the characteristics of the distribution data for the ROI 52.

When the power distribution has been calculated for each of the ROIs 52 by the distribution data calculation unit 42, the discrimination index map generation unit 44 generates a discrimination index map based on the variation in power around the most frequently occurring value in the power distribution for each of the ROIs 52.

Figure 8:
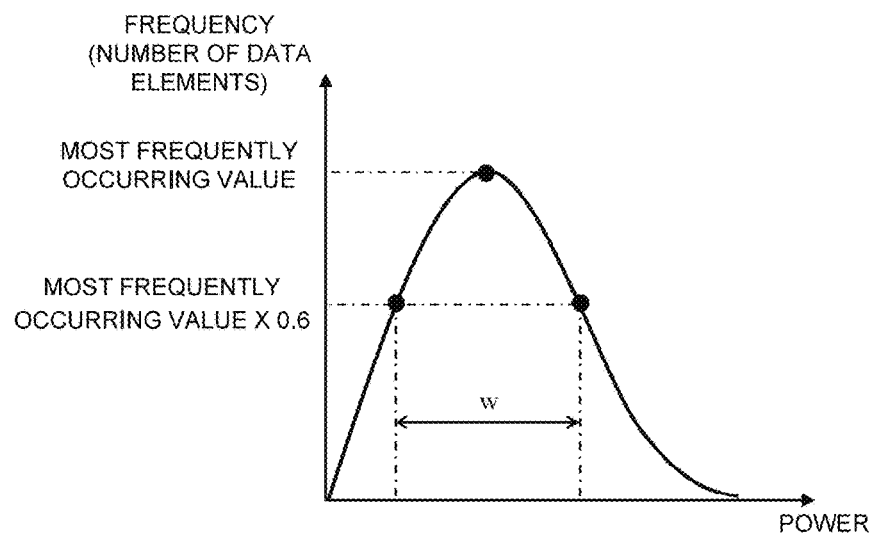
FIG. 8 is a graph showing the width of a peak constituting a most frequently occurring value in the power distribution.

FIG. 8 is a graph showing the power distribution of a certain data element. The discrimination index map generation unit 44 first identifies the most frequently occurring value in the power distribution. The discrimination index map generation unit 44 then determines a discrimination index to be assigned to a corresponding ROI 52 based on the width w of the peak including the most frequently occurring value in the graph. Specifically, the discrimination index is determined such that the larger the width w is, the larger the discrimination index becomes. In other words, the discrimination index is determined such that the smaller the width w is, the smaller the discrimination index becomes.

Although, in the present embodiment, the width w of the peak is assumed to be the difference between two power values each having the frequency determined based on the most frequently occurring value (specifically, the difference between two power values, each obtained by multiplying the most frequently occurring value by 0.6), the width w of the peak may be calculated by using other indices. For example, the above value of 0.6 may be another value.

As described above, in the graph showing the power distribution in the ROI 52*a* in the blood flow region A (see FIG. 5A), the width w of the peak including the most frequently occurring value is quite large. On the other hand, in the graph showing the power distribution in the ROI 52*b* in the background region B (see FIG. 5B), the width w of the peak including the most frequently occurring value is much smaller. Further, although the graph showing the power distribution in the ROI 52*c* in the blooming region C (see FIG. 5C) includes the wide peak, as for the peak constituting the most frequently occurring value, the width w is quite small like that in the background region B. That is, by determining the discrimination index based on the width w of the peak constituting the most frequently occurring value, it is possible to assign a discrimination index with a larger value to the ROI 52*a* in the blood flow region A and a discrimination index with a smaller value to the ROI in the blooming region C as well as to the ROI in the background region B.

When the velocity distribution is calculated for each of the ROIs 52 by the distribution data calculation unit 42, the discrimination index map generation unit 44 generates a discrimination index map based on the variation in velocity around the most frequently occurring value in the velocity distribution for each of the ROIs 52. Like in the case of the power distribution, the discrimination index map generation unit 44 determines a discrimination index to be assigned to a corresponding ROI 52 based on the width w of the peak including the most frequently occurring value in the velocity distribution graph. However, as for the velocity distribution, contrary to the case of the power distribution, the discrimination index map generation unit 44 determines the discrimination index such that the smaller the width w is, the larger the discrimination index becomes. In other words, it determines the discrimination index such that the larger the width w is, the smaller the discrimination index becomes.

As described above, in the graph showing the velocity distribution in the ROI 52*a* in the blood flow region A (see FIG. 6A), the width w of the peak including the most frequently occurring value is quite small. On the other hand, in the graph showing the velocity distribution in the ROI 52*b* in the background region B (see FIG. 6B), the width w of the peak including the most frequently occurring value is much larger. Further, in the graph showing the velocity distribution in the ROI 52*c* in the blooming region C (see FIG. the width w of the peak including the most frequently occurring value is smaller than that in the background region B but is larger than that in the blood flow region A. That is, by determining the discrimination index based on the width w of the peak constituting the most frequently occurring value, it is possible to assign a discrimination index with a larger value to the ROI 52*a* in the blood flow region A and a discrimination index with a smaller value to the ROI in the blooming region C as well as to the ROI in the background region B.

When the velocity dispersion distribution is calculated for each of the ROIs 52 by the distribution data calculation unit 42, the discrimination index map generation unit 44 generates a discrimination index map based on the variation in velocity dispersion around the most frequently occurring value in the velocity dispersion distribution for each of the ROIs 52. Like in the cases of the power distribution and the velocity distribution, the discrimination index map generation unit 44 determines a discrimination index to be assigned to a corresponding ROI 52 based on the width w of the peak including the most frequently occurring value in the dispersion distribution graph. As for the dispersion distribution, contrary to the case of the power distribution, a discrimination index is determined such that smaller the width w is, the larger the discrimination index becomes, like in the case of the velocity distribution. In other words, the discrimination index is determined such that the larger the width w is, the smaller the discrimination index becomes.

As described above, in the graph showing the dispersion distribution in the ROI 52*a* in the blood flow region A (see FIG. 7A), the width w of the peak including the most frequently occurring value is quite small. On the other hand, in the graph showing the dispersion distribution in the ROI 52*b* in the background region B (see FIG. 7B), the width w of the peak including the most frequently occurring value is much larger. Further, in the graph showing the dispersion distribution in the ROI 52*c* in the blooming region C (see FIG. 7C), the width w of the peak including the most frequently occurring value is smaller than that in the background region B but is larger than that in the blood flow region A. That is, again, by determining the discrimination index based on the width w of the peak constituting the most frequently occurring value, it is possible to assign a discrimination index with a larger value to the ROI 52*a* in the blood flow region A and a discrimination index with a smaller value to the ROI in the blooming region C as well as to the ROI in the background region B.

Figure 9:
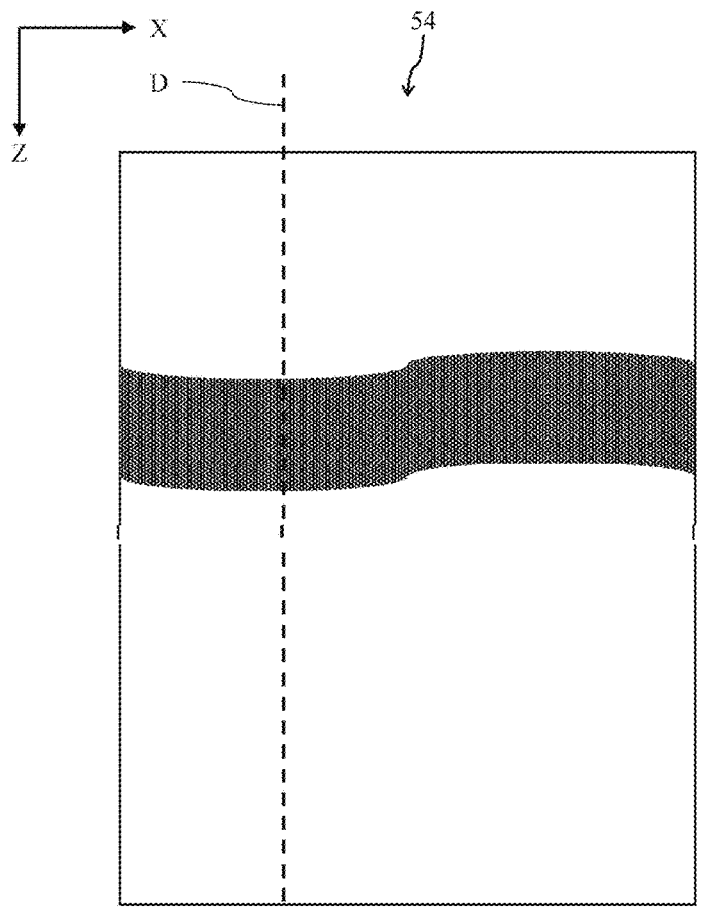
FIG. 9 is a conceptual diagram showing an example of a discrimination index map.
Figure 10:
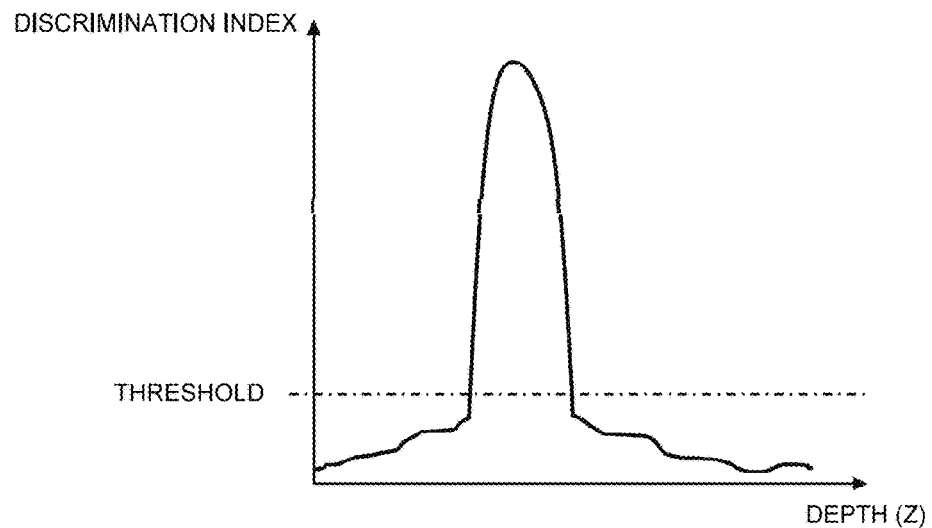
FIG. 10 is a graph showing a change in discrimination index along line D in FIG. 9.

FIG. 9 is a conceptual diagram showing an example of a discrimination index map 54 generated by the discrimination index map generation unit 44. FIG. 10 is a graph showing a change in discrimination index along line D parallel to the z-axis direction in FIG. 9. In the discrimination index map 54, the discrimination index for the portion corresponding to the blood flow region A is larger, while the discrimination indices for the portions corresponding to the background region B and the blooming region C are smaller.

In the present embodiment, the discrimination index map generation unit 44 performs a process of normalizing the discrimination index assigned to each data element. For example, the discrimination index map generation unit 44 performs, for data elements each having a discrimination index below a predetermined threshold (see FIG. 10) in the discrimination index map 54, a process of setting the discrimination index to 0 as the normalization process. This is performed because the data element having the discrimination index having a value below the threshold (that is, a fairly small value) is unlikely to be a data element corresponding to the blood flow region A.

In addition, depending on the method of calculation, the discrimination index may have a considerably large value, such as 10,000. In other words, the discrimination index may have a wide range of values. When the variation in discrimination index is large, it may be difficult to properly discriminate between the blood flow region A and the other regions (the background regions B and the blooming regions C) in the process carried out by the blood flow image forming unit 46 described below. The discrimination index map generation unit 44 therefore converts the discrimination index for each data element in the discrimination index map 54 to a value between 0 and 1 in the normalization process. The discrimination index map 54 obtained by converting (normalizing) the discrimination indices in this manner will be referred to as a gain map. In the present embodiment, the discrimination index map generation unit 44 normalizes (converts) the discrimination indices by using a gain function. For example, the normalization processing is expressed by Equation 1 below.

[Equation 1]

$$g(x,z)=G(d(x,z)) \quad \text{(Equation 1)}$$

Figure 11:
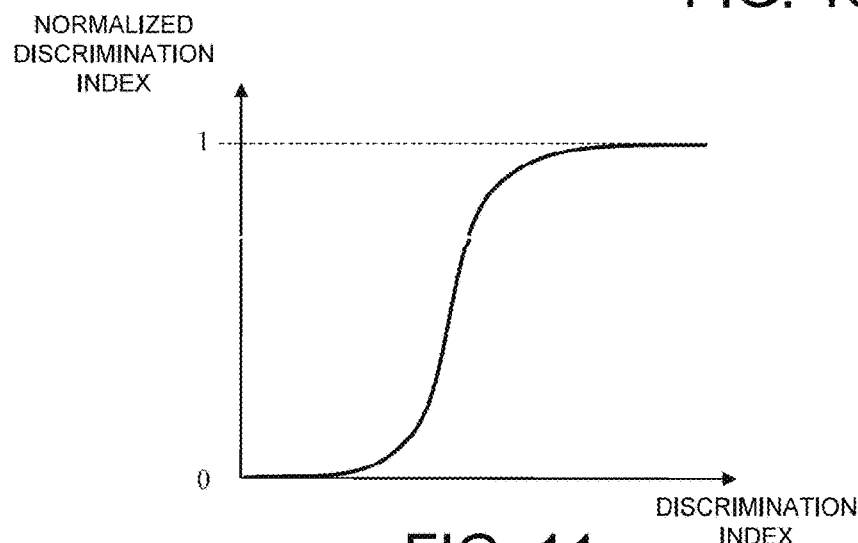
FIG. 11 is a graph showing a relationship between discrimination index and gain.

In Equation 1, a data element located at x along the X-axis and z along the Z-axis is defined by the coordinates (x, z). In addition, g(x, z) represents a discrimination index (normalized discrimination index) of the data element (x, z) in the gain map, and d(x, z) represents a discrimination index of the data element (x, z) before normalization. G(d(x, z)) represents the gain function. The gain function may be a sigmoid function, as shown in FIG. 11, for example.

In the present embodiment, the discrimination index for each data element included in the gain map has a value of 0 to 1. In particular, in a gain map 56, the data element corresponding to the blood flow region A has a discrimination index having a value of 1 or close to 1, while the data element corresponding to the background region B or the blooming region C has a discrimination index having a value of 0 or close to 0.

The blood flow image forming unit 46 forms a blood flow image in which the blood flow in the subject is represented based on the Doppler signal obtained through the processing by the Doppler processing unit 40 and the discrimination index map generated by the discrimination index map generation unit 44. In the present embodiment, the power map, the velocity map, or the dispersion map has been calculated by the distribution data calculation unit 42, and the blood flow image forming unit 46 thus forms a blood flow image based on the power map, the velocity map, or the dispersion map, and the discrimination index map.

Figure 12:
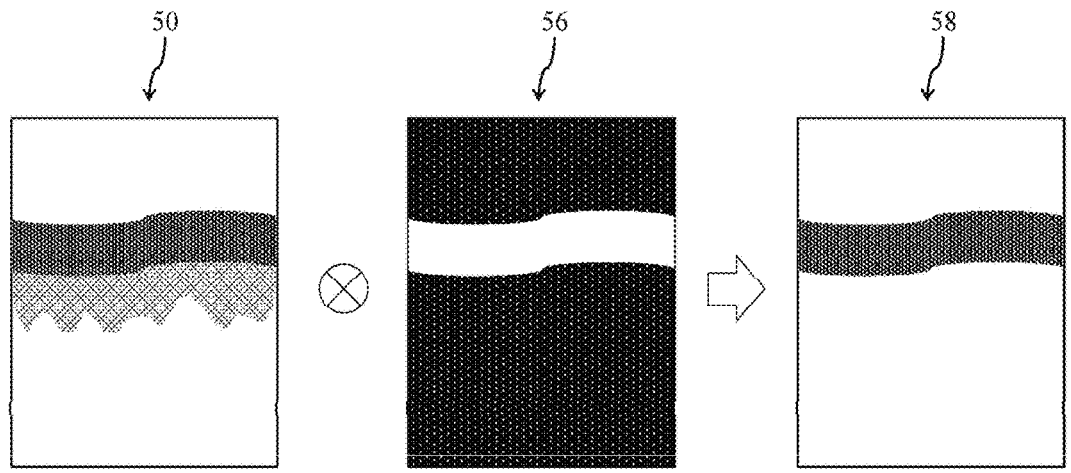
FIG. 12 is a conceptual diagram showing a process of forming a blood flow image based on a power image and a gain map.

Specifically, as shown in FIG. 12, the blood flow image forming unit 46 multiplies the power map 50 by the gain map 56 (normalized discrimination index map) to thereby form a power image 58 as a blood flow image with reduced blooming artifacts. Multiplying the power map 50 by the gain map 56 means multiplying the power of a data element in the power map 50 by the discrimination index (0 to 1) of that data element in the gain map 56 and setting the calculation result as a signal value of the data element in the power image 58. As described above, in the gain map 56, the data element corresponding to the blood flow region A has a discrimination index having a value of 1 or close to 1, and the data element corresponding to the background region B or the blooming region C has a discrimination index having a value of 0 or close to 0. Therefore, in the power image 58, as for the signal value of the data element corresponding to the blood flow region A, the power of that data element in the power map 50 is maintained without large changes, while the signal value of the data element corresponding to the background region B or the blooming region C becomes almost 0.

Similarly, the blood flow image forming unit 46 may multiply the velocity map but not the power map 50 by the gain map 56 to thereby obtain a velocity image as a blood flow image with reduced blooming artifacts. In addition, the blood flow image forming unit 46 may multiply the dispersion map but not the power map 50 by the gain map 56 to thereby obtain a dispersion image as a blood flow image with reduced blooming artifacts.

Figure 13A:
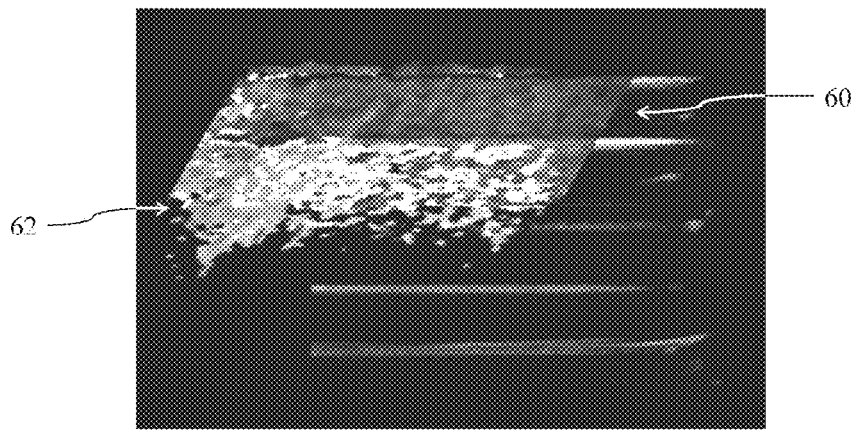
FIG. 13A is a diagram showing an example of a blood flow image without a blooming artifact reduction process according to the embodiment.
Figure 13B:
FIG. 13B is a diagram showing an example of a blood flow image when the blooming artifact reduction process according to the embodiment is performed.

As described above, the present embodiment makes it possible to obtain the blood flow image (power image or color Doppler image (velocity image or dispersion image)) with reduced blooming artifacts. FIGS. 13A and 13B show the effect of the present embodiment. FIG. 13A is a diagram showing an example of a power image without the above blooming artifact reduction process according to the present embodiment. In FIG. 13A, a blooming artifact 62 is observed on the underside of a blood vessel 60. FIG. 13B is a diagram showing an example of a power image when the blooming artifact reduction process according to the present embodiment is performed. FIG. 13B shows that the blooming artifact 62, which is included in FIG. 13A, is significantly reduced.

The display control unit 26 displays the blood flow image formed by the Doppler image forming unit 24 on the display 28. For example, the display control unit 26 superimposes the blood flow image on the B-mode image formed by the tomographic image forming unit 22 and displays the resulting image on the display 28.

Figure 14:
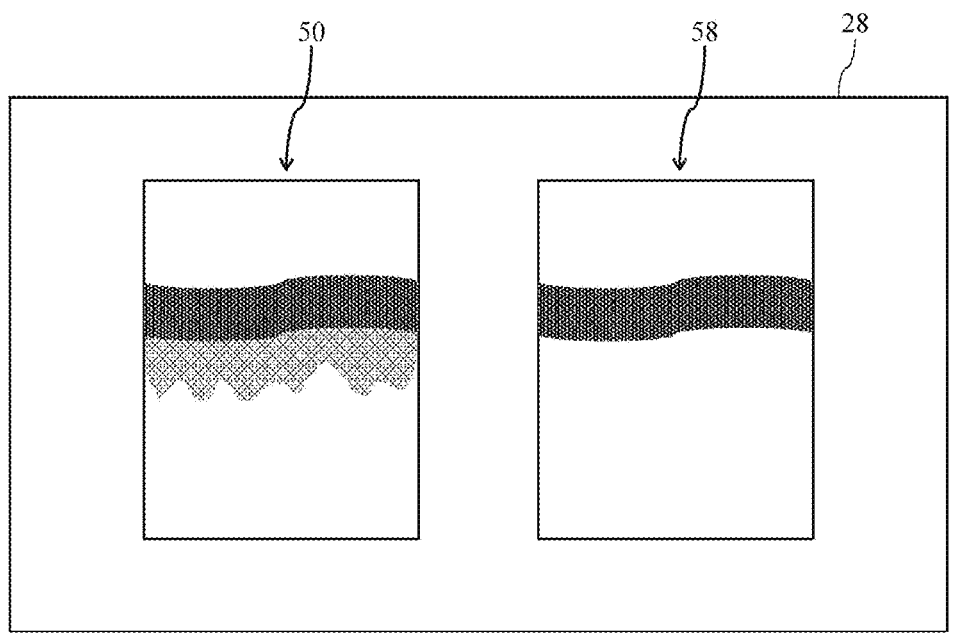
FIG. 14 is a diagram showing a display example of the blood flow images.

The display control unit 26 may display the blood flow image with reduced blooming artifacts and the blood flow image without the blooming artifact reduction process on the display 28. For example, as shown in FIG. 14, the display control unit 26 may display the power image 58 with reduced blooming artifacts and the power image where the blooming artifacts are not reduced (that is, the power map 50) side by side. This allows the user not only to see the extent to which blooming artifacts have been reduced, but also to confirm the original power image which is not subjected to the blooming artifact reduction process.

Figure 15:
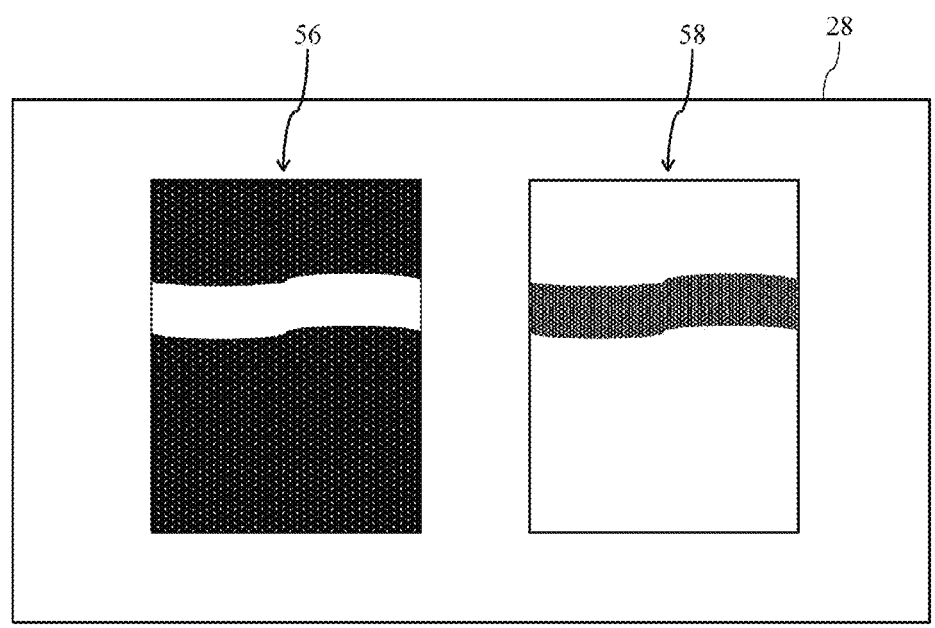
FIG. 15 is a diagram showing a display example of the gain map.

The display control unit 26 may also display the discrimination index map formed by the discrimination index map generation unit 44 on the display 28. For example, as shown in FIG. 15, the display control unit 26 may display the power image 58 with reduced blooming artifacts and the gain map 56 which has been used to obtain that power image 58 side by side. The display control unit 26 may display the discrimination index map before normalization, instead of the gain map 56. This allows the user to confirm the gain map 56 (or the discrimination index map) which has been used to reduce the blooming artifacts.

For the Doppler image forming unit 24, it may be possible for the user to set parameters for the process of forming the blood flow image according to the present embodiment; that is, parameters for the blooming artifact reduction process. Possible parameters include, for example, parameters indicating the size of the ROI 52 (see FIG. 4) to be set by the distribution data calculation unit 42 and parameters to be used for normalization of the discrimination index performed by the discrimination index map generation unit 44, but are not limited to these. The parameters related to the normalization of the discrimination index include, for example, the threshold shown in FIG. 10 or the gain value of the sigmoid function (see FIG. 11), which is the gain function.

Figure 16:
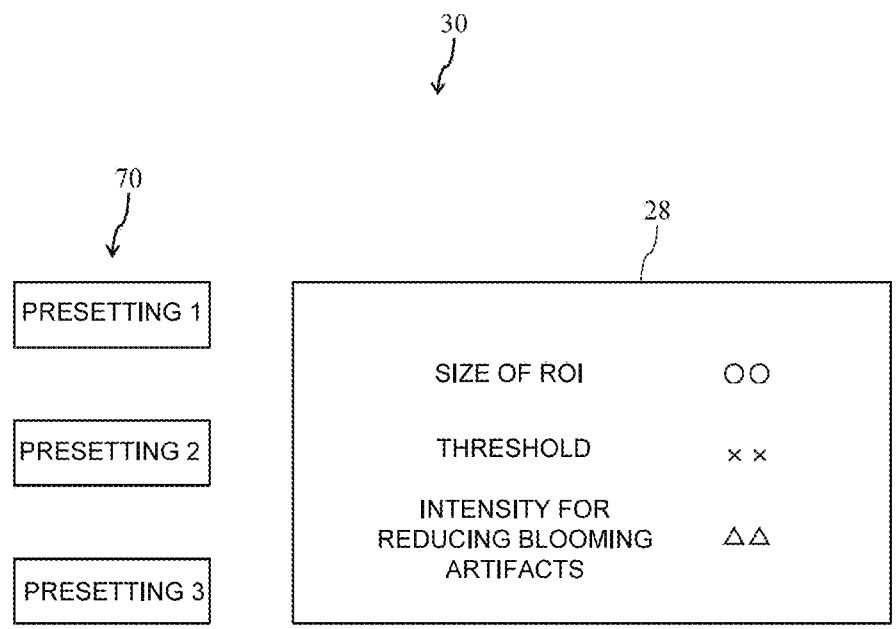
FIG. 16 is a diagram showing an example of a user interface.

For example, as shown in FIG. 16, a plurality of combinations of these parameters may be set in advance as presettings, and a plurality of preset buttons 70 corresponding to the presettings may be provided as the input interface 30. When the user selects and operates a desired one of the preset buttons 70, the Doppler image forming unit 24 sets parameters indicated by the presetting corresponding to the operated preset button 70 as parameters for the blooming artifact reduction process. The display control unit 26 may display a set value for each parameter on the display 28. The display panel may also be a touch panel, and each parameter may be set individually by operating the display 28.

Although, in the embodiment described above, the discrimination index map generation unit 44 generates the discrimination index map using any one of the power map, the velocity map, and the dispersion map calculated by the distribution data calculation unit 42, the distribution data calculation unit 42 may calculate the power map, the velocity map, and the dispersion map, and then the discrimination index map generation unit 44 may generate the discrimination index map based on the power map, the velocity map, and the dispersion map.

In this case, the discrimination index map generation unit 44 estimates the spectrum of Doppler shift ω for each data element based on the power, the velocity, and the velocity dispersion calculated for each data element. Specifically, first, the discrimination index map generation unit 44 assumes that the spectrum of Doppler shift ω is a Gaussian distribution and sets the Gaussian $S_0(\omega)$ as shown in Equation 2 below.

[Equation 2]

$$S_0(\omega) = \frac{1}{\sqrt{2\pi} \cdot \sigma} \exp\left\{-\frac{(\omega - \omega_0)^2}{2\sigma^2}\right\} \qquad \text{(Equation 2)}$$

In Equation 2, $\omega_0$ is the velocity of a data element and $\sigma$ is the velocity dispersion of the data element.

The discrimination index map generation unit 44 then calculates parameter A by dividing the power by the total power of the Gaussian $S_0(\omega)$, as shown in Equation 3 below.

[Equation 3]

$$A = \frac{P}{\int S_0(\omega) d\omega} \qquad \text{(Equation 3)}$$

In Equation 3, P is the power of the data element.

Finally, the discrimination index map generation unit 44 estimates the spectrum S(ω) of the Doppler shift ω by the following Equation 4.

[Equation 4]

$$S(\omega) = A \cdot \frac{1}{\sqrt{2\pi} \cdot \sigma} \exp\left\{-\frac{(\omega - \omega_0)^2}{2\sigma^2}\right\} \qquad \text{(Equation 4)}$$

Figure 17:
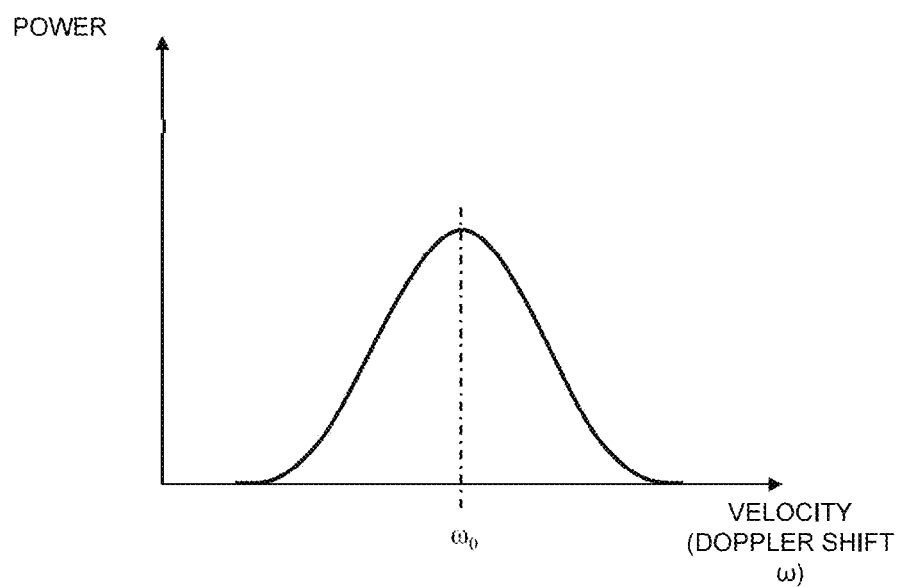
FIG. 17 is a graph showing a spectrum of an estimated Doppler shift.

The spectrum S(ω) of the Doppler shift ω estimated in this way results in a graph including an integral value P, as shown in FIG. 17.

It is important here to note that the spectrum S(ω) of a data element in the blood flow region A, the spectrum S(ω) of a data element in the background region B, and the spectrum S(ω) of a data element in the blooming region C have different characteristics from one another.

Figure 18A:
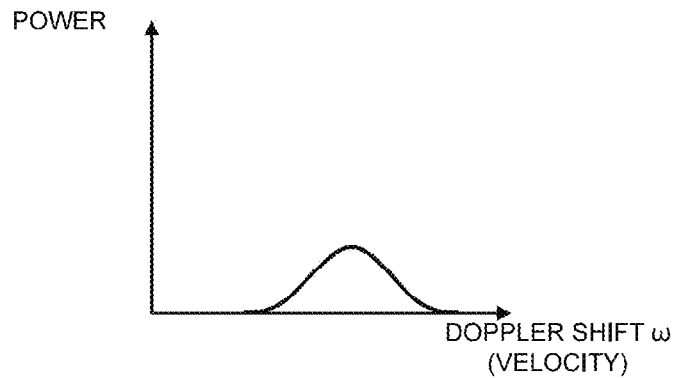
FIG. 18A is a graph showing an example of a spectrum of a Doppler shift of a data element in the blood flow region.
Figure 18B:
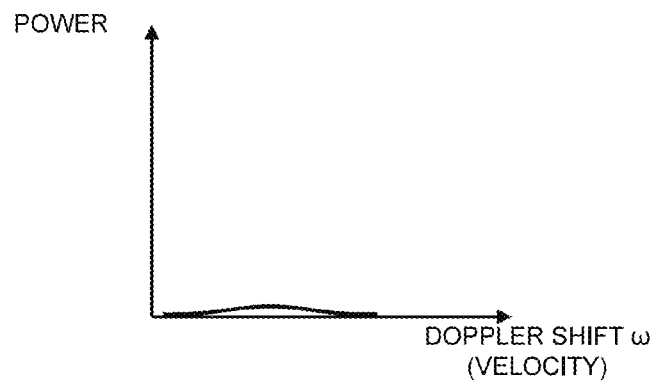
FIG. 18B is a graph showing an example of a spectrum of a Doppler shift of a data element in the background region.
Figure 18C:
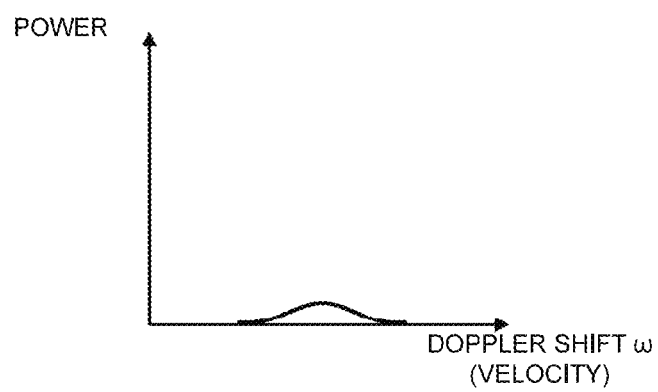
FIG. 18C is a graph showing an example of a spectrum of a Doppler shift of a data element in the blooming region.

FIG. 18A is a graph showing an example of the spectrum S(ω) of a data element included in the blood flow region A. FIG. 18B is a graph showing an example of the spectrum S(ω) of a data element included in the background region B. FIG. 18C is a graph showing an example of the spectrum S(ω) of a data element included in the blooming region C. In each of FIGS. 18A to 18C, the horizontal axis represents Doppler shift ω, and the vertical axis represents power.

The spectrum S(ω) of the data element included in the blood flow region A has a peak at a larger value of Doppler shift ω and has larger power than the spectra S(ω) of the data elements in the background region B and the blooming region C. Therefore, the discrimination index map generation unit 44 calculates the first-order moment such that the spectrum S(ω) having a peak at a larger value of Doppler shift ω has a larger value of the first-order moment and sets the resulting first-order moment as the discrimination index for the data element. The first-order moment $M_1$ of the spectrum S(ω) is calculated by the following Equation 5.

[Equation 5]

$$M_1 = \int \omega \cdot S(\omega) d\omega \qquad \text{(Equation 5)}$$

This makes it possible to assign the discrimination index with a larger value to the data element included in the blood flow region A and the discrimination index with a smaller value to those included in the blooming region C and the background region B. When assigning the discrimination index based on the spectrum S(ω) of Doppler shift ω, the distribution data calculation unit 42 does not need to set the ROIs 52 or obtain the distribution data for each ROI 52 because this process is performed for each data element, as described above.

Although, in this embodiment, the first-order moment $M_1$ of the spectrum S(ω) has been used as the discrimination index, the discrimination index may be calculated in consideration of the second and higher moments as well. Any nth-order moment $M_n$ is calculated by the following Equation 6.

[Equation 6]

$$M_n = \int \omega^n \cdot S(\omega) d\omega \qquad \text{(Equation 6)}$$

Figure 19:
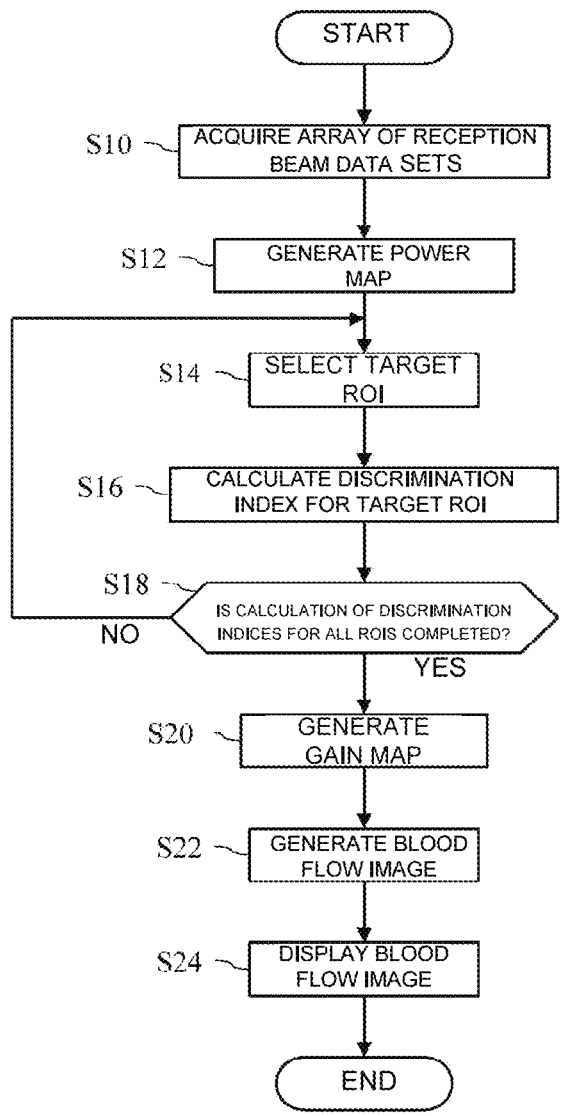
FIG. 19 is a flowchart showing a flow of processing in the ultrasonic diagnostic device according to the embodiment.
Figure 20:
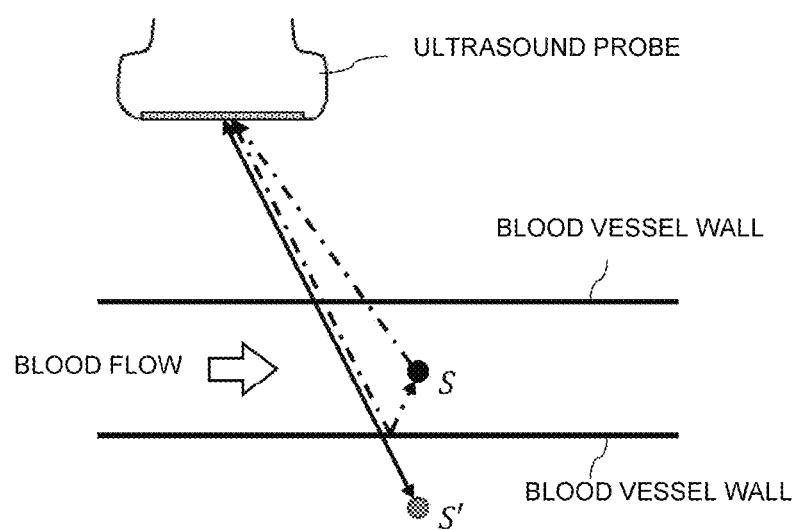
FIG. 20 is a diagram showing an example of a cause of blooming artifacts.

The outline of the ultrasonic diagnostic device 10 according to the embodiments is as described above. The process flow of the ultrasonic diagnostic device 10 will be described below with reference to the flowchart shown in FIG. 19.

In step S10, the transmission unit 14 provides the probe 12 with a plurality of transmission signals, and the probe 12 then transmits ultrasonic waves to the subject based on these signals. The probe 12 receives waves reflected from the subject and transmits a plurality of reception signals to the reception unit 16. The reception unit 16 generates an array of reception beam data sets based on the plurality of reception signals.

In step S12, the Doppler processing unit 40 generates a Doppler signal based on each reception beam data set constituting the array of reception beam data sets. The distribution data calculation unit 42 calculates power, velocity, or velocity dispersion for each data element based on the Doppler signal for each data element. Here, the distribution data calculation unit 42 is assumed to calculate power of the data elements to thereby generate the power map 50 (see FIG. 4). The distribution data calculation unit 42 also sets a plurality of ROIs 52 in the power map 50 to obtain the power distribution for each of the ROIs 52.

In step S14, the discrimination index map generation unit 44 selects a target ROI from the plurality of ROIs 52 set in step S12.

In step S16, the discrimination index map generation unit 44 calculates a discrimination index for the target ROI (that is, the data elements included in the target ROI) based on the power distribution of the target ROI selected in step S14.

In step S18, the discrimination index map generation unit 44 determines whether calculation of the discrimination indices for all the ROIs 52 set in step S12 is complete. When there remains any ROI 52 for which the discrimination index has not been calculated, the process returns to step S14, and in step S14, the discrimination index map generation unit 44 selects as the target ROI that ROI 52 for which the discrimination index has not been calculated. When calculation of discrimination indices for all the ROIs 52 is completed, the process proceeds to step S20.

In step S20, the discrimination index map generation unit 44 normalizes the discrimination index calculated for each data element to generate the gain map 56.

In step S22, the blood flow image forming unit 46 multiplies the power map 50 generated in step S12 by the gain map 56 generated in step S20 to thereby form the power image 58 as the blood flow image with reduced blooming artifacts.

In step S24, the display control unit 26 superimposes the Doppler image formed in step S22 on the B-mode image formed by the tomographic image forming unit 22 and displays the resulting image on the display 28.

Although the blood flow image forming device according to the present disclosure has been described, the ultrasonic diagnostic device according to the present disclosure is not limited to the above embodiments, and various changes can be made without departing from the spirit of the present disclosure.

For example, although, in the above embodiments, the blood flow image forming device has been the ultrasonic diagnostic device 10, the blood flow image forming device is not limited to the ultrasonic diagnostic device 10 and may be other computers. In this case, a computer which is the blood flow image forming device has the functions as the Doppler image forming unit 24. Specifically, the computer, which is the blood flow image forming device, acquires the array of reception beam data sets from the ultrasonic diagnostic device (in this case, an interface of the computer corresponds to the reception beam data acquisition unit), and the Doppler image forming unit 24 performs the above processing based on this array of reception beam data sets to thereby form a blood flow image with reduced blooming artifacts.

The invention claimed is:

1. A blood flow image forming device comprising:
a reception beam data acquisition unit that acquires an array of reception beam data sets generated based on signals received from an ultrasound probe that transmits and receives ultrasonic waves with respect to a beam scanning plane in a subject, the array of reception beam data sets corresponding to transmission beams forming the beam scanning plane;
a distribution data calculation unit that calculates, for each of a plurality of regions of interest that are set in a two-dimensional data space composed of the array of reception beam data sets, distribution data that relates to at least one of power distribution of a Doppler signal obtained from the reception beam data set, velocity distribution of tissue in the subject, and velocity dispersion distribution of tissue in the subject, based on the array of reception beam data sets;
a discrimination index map generation unit that generates a discrimination index map indicating the likelihood of being a blood flow region in the two-dimensional data space based on the distribution data for each of the regions of interest; and
a blood flow image forming unit that forms a blood flow image in which a blood flow in the subject is represented based on the Doppler signal obtained from the array of reception beam data sets and the discrimination index map.

2. The blood flow image forming device according to claim 1, wherein the discrimination index map generation unit generates the discrimination index map based on variation in power around a most frequently occurring value in the power distribution for each of the regions of interest, variation in velocity around a most frequently occurring value in the velocity distribution for each of the regions of interest, or variation in velocity dispersion around a most frequently occurring value in the velocity dispersion distribution for each of the regions of interest.

3. The blood flow image forming device according to claim 1, wherein
the discrimination index map generation unit normalizes a discrimination index included in the discrimination index map, and
the blood flow image forming unit forms the blood flow image based on the Doppler signal and the discrimination index map having the normalized discrimination index.

4. The blood flow image forming device according to claim 3, wherein parameters for a process of forming the blood flow image, including parameters representing the size of the region of interest and parameters for the normalization, are configurable by the user.

5. The blood flow image forming device according to claim 1, further comprising a display control unit that displays the discrimination index map on a display unit.

6. A blood flow image forming device comprising:
a reception beam data acquisition unit that acquires an array of reception beam data sets generated based on signals received from an ultrasound probe that transmits and receives ultrasonic waves with respect to a beam scanning plane in a subject, the array of reception beam data sets corresponding to transmission beams forming the beam scanning plane;
a distribution data calculation unit that calculates, for each of a plurality of regions of interest that are set in a two-dimensional data space composed of the array of reception beam data sets, power distribution of a Doppler signal obtained from the reception beam data set, velocity distribution of tissue in the subject, and velocity dispersion distribution of tissue in the subject, based on the array of reception beam data sets;
a discrimination index map generation unit that generates a discrimination index map indicating the likelihood of being a blood flow region in the two-dimensional data space based on the power distribution, the velocity distribution, and the dispersion distribution; and
a blood flow image forming unit that forms a blood flow image in which a blood flow in the subject is represented based on the Doppler signal obtained from the array of reception beam data sets and the discrimination index map.

7. A computer-readable, non-transitory storage medium storing instructions that are executable by a computer, the instructions causing the computer to perform:
- a reception beam data acquisition step of acquiring an array of reception beam data sets generated based on signals received from an ultrasound probe that transmits and receives ultrasonic waves with respect to a beam scanning plane in a subject, the array of reception beam data sets corresponding to transmission beams forming the beam scanning plane;
- a distribution data calculation step of calculating, for each of a plurality of regions of interest that are set in a two-dimensional data space composed of the array of reception beam data sets, distribution data that relate to at least one of power distribution of a Doppler signal obtained from the reception beam data set, velocity distribution of tissue in the subject, and velocity dispersion distribution of tissue in the subject, based on the array of reception beam data sets;
- a discrimination index map generation step of generating a discrimination index map indicating the likelihood of being a blood flow region in the two-dimensional data space based on the distribution data for each of the regions of interest; and
- a blood flow image forming step of forming a blood flow image in which a blood flow in the subject is represented based on the Doppler signal obtained from the array of reception beam data sets and the discrimination index map.

8. A computer-readable, non-transitory storage medium storing instructions that are executable by a computer, the instructions causing the computer to perform:
- a reception beam data acquisition step of acquiring an array of reception beam data sets generated based on signals received from an ultrasound probe that transmits and receives ultrasonic waves with respect to a beam scanning plane in a subject, the array of reception beam data sets corresponding to transmission beams forming the beam scanning plane;
- a distribution data calculation step of calculating, for each of a plurality of regions of interest that are set in a two-dimensional data space composed of the array of reception beam data sets, power distribution of a Doppler signal obtained from the reception beam data set, velocity distribution of tissue in the subject, and velocity dispersion distribution of tissue in the subject, based on the array of reception beam data sets;
- a discrimination index map generation step of generating a discrimination index map indicating the likelihood of being a blood flow region in the two-dimensional data space based on the power distribution, the velocity distribution, and the dispersion distribution; and
- a blood flow image forming step of forming a blood flow image in which a blood flow in the subject is represented based on the Doppler signal obtained from the array of reception beam data sets and the discrimination index map.

* * * * *